(12) United States Patent
Kim et al.

(10) Patent No.: US 7,585,962 B2
(45) Date of Patent: Sep. 8, 2009

(54) MULTIMERIZED ENHANCER DOMAINS FOR CELL-SPECIFIC EXPRESSION

(75) Inventors: Kwang-Soo Kim, Lexington, MA (US); Ole Isacson, Cambridge, MA (US); Dong-Youn Hwang, Watertown, MA (US)

(73) Assignee: The McLean Hospital Corporation, Belmont, MA (US)

( * ) Notice: Subject to any disclaimer, the term of this patent is extended or adjusted under 35 U.S.C. 154(b) by 875 days.

(21) Appl. No.: 10/277,345

(22) Filed: Oct. 21, 2002

(65) Prior Publication Data

US 2003/0113918 A1    Jun. 19, 2003

Related U.S. Application Data

(60) Provisional application No. 60/343,780, filed on Oct. 19, 2001.

(51) Int. Cl.
*C07H 21/04*   (2006.01)
*C12P 21/06*   (2006.01)

(52) U.S. Cl. ..................................... 536/24.1; 435/69.1

(58) Field of Classification Search ........................ None
See application file for complete search history.

(56) References Cited

U.S. PATENT DOCUMENTS

| | | | |
|---|---|---|---|
| 4,983,518 A | 1/1991 | Schaffner et al. | |
| 5,665,567 A | 9/1997 | Eichner et al. | |
| 6,281,009 B1 | 8/2001 | Boyce | |

FOREIGN PATENT DOCUMENTS

| | | | |
|---|---|---|---|
| WO | WO 90/01550 | 2/1990 | |
| WO | WO 01/28994 | * 4/2001 | |

OTHER PUBLICATIONS

Schimmel et al. 4.5 kb or the rat tyrosine hydroxylase 5' flanking sequence directs tissue specific expression during development and contains consensus sites for multiple transcription factors. Molecular Brain Research (1999) vol. 74, pp. 1-14.*
Afar et al., "Positive and negative elements contribute to the cell-specific expression of the rat dopamine beta-hydroxylase gene," *Mol. Brain Res.* 36:79-92 (1996).
Castillo et al., "Dopamine biosynthesis is selectively abolished in substantia nigra/ventral tegmental area but not in hypothalamic neurons in mice with targeted disruption of the Nurr1 gene," *Mol. and Cell. Neurosci.* 11:36-46 (1998).
Hoyle et al., "Cell-specific expression from the human dopamine beta-hydroxylase promoter in transgenic mice is controlled via a combination of positive and negative regulatory elements," *J. Neurosci.* 14:2455-2463 (1994).
Ishiguro et al., "Neuron-specific expression of the human dopamine beta-hydroxylase gene requires both the cAMP-response element and a silencer region," *J. Biol. Chem.* 268:17987-17994 (1993).
Ishiguro et al., "Identification of a negative regulatory element in the 5'-flanking region of the human dopamine beta-hydroxylase gene," *Mol. Brain Res.* 34:251-261 (1995).
Kim et al., "Both the basal and inducible transcription of the tyrosine hydroxylase gene are dependent upon a cAMP response element," *J. Biol. Chem.* 268:15689-15695 (1993).
Kim et al., "The cell-specific silencer region of the human dopamine beta-hydroxylase gene contains several negative regulatory elements," *J. Neurochem.* 71:41-50 (1998).
Kim et al., "The cAMP-dependent protein kinase regulates transcription of the dopamine beta-hydroxylase gene," *J. Neurosci.* 14:7200-7207 (1994).
Kim et al., "Paired-like homeodomain protein, Phox2a, makes multiple contacts on the 5' promoter and critically controls dopamine β-hydroxylase (DBH) gene transcription," *Soc. Neurosci. Abstr.* 24:1265 (1998).
Kim et al., "Noradrenergic-specific transcription of the dopamine β-hydroxylase gene requires synergy of multiple cis-acting elements including at least two Phox2a-binding sites," *J. Neurosci.* 18:8247-8260 (1998).
Kim et al., "Identification and functional characterization of cell-specific and general cis-regulatory elements residing in the 5' proximal region of the human dopamine α-hydroxylase (D.B.H.) gene," *Soc. Neurosci. Abstr.* 23:352 (1997).
Kim et al., "A previously undescribed intron and extensive 5' upstream sequence, but not Phox2a-mediated transactivation, are necessary for high level cell type-specific expression of the human norepinephrine transporter gene," *J. Biol. Chem.* 274:6507-6518 (1999).
Kobayashi et al., "Functional and high level expression of human dopamine beta-hydroxylase in transgenic mice," *J. Biol. Chem.* 269:29725-29731 (1994).
Kobayashi et al., "Human dopamine beta-hydroxylase gene: two mRNA types having different 3'-terminal regions are produced through alternative polyadenylation," *Nucleic Acid Res.* 17:1089-1102 (1989).
Kordower et al., "Neurodegeneration prevented by lentiviral vector delivery of GDNF in primate models of Parkinson's disease," *Science* 290:767-773 (2000).
Min et al., "5' upstream DNA sequence of the rat tyrosine hydroxylase gene directs high-level and tissue-specific expression to catecholaminergic neurons in the central nervous system of transgenic mice," *Mol. Brain Res.* 27:281-289 (1994).
Morita et al., "The 5'-flanking region of the human dopamine beta-hydroxylase gene promotes neuron subtype-specific gene expression in the central nervous system of transgenic mice," *Mol. Brain Res.* 17:239-244 (1993).
Pattyn et al., "The homeobox gene Phox2B is essential for the development of autonomic neural crest derivatives," *Nature* 399:366-370 (1999).

(Continued)

*Primary Examiner*—Nancy Vogel
*Assistant Examiner*—Catherine Hibbert
(74) *Attorney, Agent, or Firm*—Clark & Elbing LLP; Michael J. Belliveau

(57) ABSTRACT

The invention features an enhancer cassette and methods of its use. The enhancer cassette has the formula $[X-Y]_n$, wherein each X is independently a cell type-specific enhancer element; Y is absent or is a mono or polynucleotide that has between one and thirty nucleotides; and n is an integer between five and fifty, inclusive.

5 Claims, 7 Drawing Sheets

OTHER PUBLICATIONS

Sabban et al., "Multiple pathways in regulation of dopamine beta-hydroxylase," *Adv. Pharmacol.* 42:53-56 (1998).

Saucedo-Cardenas et al., "Nurr1 is essential for the induction of the dopaminergic phenotype and the survival of ventral mesencephalic late dopaminergic precursor neurons," *Proc. Natl. Acad. Sci. USA* 95:4013-4018 (1998).

Seo et al., "A direct role of the homeodomain proteins Phox2a/2b in noradrenaline neurotransmitter identity determination," *J. Neurochem.* 80:905-916 (2002).

Seo et al., "Multiple protein factors interact with the cis-regulatory elements of the proximal promoter in a cell-specific manner and regulate transcription of the dopamine beta-hydroxylase gene," *J. Neurosci.*, 16: 4102-4112, (1996).

Shaskus et al., "A negative regulatory element in the rat dopamine beta-hydroxylase gene contributes to the cell type specificity of expression," *J. Neurochem.*, 64: 52-60, (1995).

Smidt et al., "A homeodomain gene *Ptx3* has highly restricted brain expression in mesencephalic dopaminergic neurons," *Proc. Natl. Acad. Sci. USA*, 94: 13305-13310 (1997).

Stanke et al., "The Phox2 homeodomain proteins are sufficient to promote the development of sympathetic neurons," *Development*, 126: 4087-4094, (1999).

Swanson et al., "The homeodomain protein Arix interacts synergistically with cyclic AMP to regulate expression of neurotransmitter biosynthetic genes," *J. Biol. Chem.*, 272: 27382-27392, (1997).

Yang et al., "Paired-like homeodomain proteins, Phox2a and Phox2b, are responsible for noradrenergic cell-specific transcription of the dopamine β-hydroxylase gene," *J. Neurochem.* 71:1813-1826 (1998).

Zetterström et al., "Dopamine neuron agenesis in Nurr1-deficient mice," *Science* 276:248-250 (1997).

* cited by examiner

MULTIMERIZED ENHANCER DOMAINS FOR CELL-SPECIFIC EXPRESSION

CROSS-REFERENCE TO RELATED APPLICATIONS

This application claims benefit from U.S. Provisional Application No. 60/343,780 (filed Oct. 19, 2001), hereby incorporated by reference.

STATEMENT AS TO FEDERALLY SPONSORED RESEARCH

This invention was sponsored in part by RO1 Grant #MH48866 from the National Institutes of Health. The Government has certain rights to this invention.

BACKGROUND OF THE INVENTION

The invention relates to the field of cell type-specific gene expression.

Gene therapy holds promise for treating a wide variety of human metabolic diseases that are incurable or difficult to treat by more conventional procedures (reviewed in Mulligan, Science 260:926-932, 1993; Leiden, N. Eng. J. Med. 333:871-873, 1995). Gene therapy for disorders in the nervous system are particularly challenging because of the postmitotic state of most neurons, the complex nature of many brain diseases, extremely heterogeneous structure and function of different subtypes of neurons, and poorly understood control mechanisms of most brain-specific genes.

Parkinson's disease (PD), one of the most common neurodegenerative diseases in the world, is caused by specific neuronal loss of midbrain dopaminergic (DA) neurons. Gene therapy approach has great potential for treatment of PD (Costantini et al., Hum. Gene Ther. 10: 2481-2494, 1999; Constantini et al., Gene Ther. 7:93-109, 2000). For example, recent work by Kordower et al. (Science 290:767-773, 2000) demonstrated that lentiviral delivery of glial cell line-derived neurotrophic factor (GDNF) reversed functional deficits and completely prevented nigrostriatal degeneration in MPTP-treated monkey models of PD.

Based in part on the promise demonstrated the experiments such as the one described above, efficient promoter systems that can direct high level and long-term expression of therapeutic genes in a cell type-specific manner are in great need. Currently, most gene therapy procedures employ viral promoter systems such as CMV, RSV, and HSV IE promoters and have resulted in transient, high-level expression in most cell types. While transgene expression can be maintained stable at high-level under cell culture conditions, it rapidly diminishes in vivo following direct gene transfer or implantation of modified cells into target areas (During et al., Science 266:1399-1403, 1994; Palmer et al., Proc. Natl. Acad. Sci. USA 88:1330-1334, 1991). Furthermore, these viral promoters do not provide cell-type specific and controllable transgene expression. Thus it is desirable to use expression constructs that are capable of directing gene expression in differentiated neuronal cells in vivo, preferably in a cell type-specific manner.

Several studies have shown that two transcription factors, Nurr1 and Ptx3, are required for proper development and phenotypic specification of dopaminergic neurons (Smidt et al., Proc. Natl. Acad. Sci. USA 94:13305-13310, 1997; Zetterstrom et al., Science 276:248-250, 1997; Castillo et al., Mol. Cell Neurosci. 11:36-46, 1998; Saucedo-Cardenas et al., Proc. Natl. Acad. Sci. USA 95:4013-4018, 1998). Moreover, these transcription factors are selectively expressed in midbrain dopaminergic neurons.

SUMMARY OF THE INVENTION

We have discovered that an expression construct that included multiple copies of dopaminergic cell-specific enhancer domains that bind to Nurr1 and isolated from the tyrosine hydroxylase gene increased the minimal promoter activity by 100- to 200-fold in DA-positive cell lines. Moreover, we discovered that this expression construct maintained the cell-type specificity exhibited by the natural TH promoter.

Based on our findings, we postulate that placement of cell type-specific multimerized enhancer domains proximal to a transgene to be expressed will greatly increase transgene expression in a cell type-specific manner.

Accordingly, the invention features an enhancer cassette having the formula $[X-Y]_n$, wherein each X is independently a cell type-specific enhancer; Y is absent or is a mono or polynucleotide that has between one and thirty nucleotides; and n is an integer between five and fifty, inclusive. In one example, the cell type-specific enhancer is a neuronal cell type-specific enhancer such as a dopaminergic cell type-specific enhancer that binds specifically to Nurr1 or Ptx3. In one embodiment, each X be independently selected from the group consisting of 5'-TTCAGCCTGGCCTTTAAAGA-3' (SEQ ID NO: 1), 5'-TGTCTCCAAAG GTTATAGTT-3' (SEQ ID NO: 2), 5'-AAACAAAAGGTCACTTACTG-3' (SEQ ID NO: 3), and 5'-TAATCC(A/C)-3' (SEQ ID NO: 4); Y is absent or is a mono or polynucleotide that has between one and six nucleotides; and n is between five and fifty, inclusive. In other embodiments, X includes a region that shares greater than 70%, 80%, 90%, or 95% sequence identity with SEQ ID NO: 1, SEQ ID NO: 2, or SEQ ID NO: 3 and binds to human Nurr1, or shares greater than 70%, 80%, 90%, or 95% sequence identity with SEQ ID NO: 4 and binds to human Ptx3.

The enhancer cassette is useful for expressing a polynucleotide in a cell-type specific manner. To this end, the enhancer cassette can be combined with an RNA polymerase binding site and a transcription initiation site to form an expression construct. Additionally, the enhancer cassette and expression construct of the invention can each be a component of an expression vector, such as an adenoviral vector or a retroviral vector. The invention further features an isolated polynucleotide consisting essentially of SEQ ID NO: 3.

As used herein, by "nucleic acid" is meant either DNA or RNA. A "polynucleotide" may be a single-stranded or double-stranded polymer of deoxyribonucleotide or ribonucleotide bases. Unless otherwise specified, the left hand direction of the sequence of a single-stranded polynucleotide is the 5' end, and the left hand direction of double-stranded nucleic molecule is referred to as the 5' direction.

By "promoter" is meant a region of nucleic acid, upstream from a translational start codon, which is involved in recognition and binding of RNA polymerase and other proteins to initiate transcription. A "TH promoter" is one derived from the promoter region of a TH gene and that, when operably linked to a heterologous polynucleotide, is capable of initiating transcription of that molecule when present in a transcription medium capable of supporting transcription.

Exemplary transcription media include, for example, a mammalian cell (e.g., an immortalized cell), and a yeast cell. Also included are in vitro expression systems such as reconstituted expression medium composed of components required to support transcription, as are known in the art.

By "enhancer domain" or "domain" is meant a nucleic acid sequence that, when positioned proximate to a promoter and present in a transcription medium capable of supporting transcription, confers increased transcription activity relative to the transcription activity resulting from the promoter in the absence of the enhancer domain. By "enhancer cassette" is meant a nucleic acid sequence that includes an enhancer domain and, optionally, additional sequence that does not enhance transcription (e.g., spacer sequence).

By "multimerized enhancer domain" is meant two or more copies of a dopaminergic cell-specific enhancer domain. Preferably, the number of copies is between three and twenty, inclusive. The enhancer domains can be in the same or opposite orientation, and can be contiguous or noncontiguous. In expression constructs having two different enhancer domains (e.g., domain A and domain B), the orientation and the 5' to 3' order (e.g., 5'-AABB-3' vs. 5'-ABAB-3') are not limitations to the invention.

By "operably linked" is meant that a polynucleotide to be transcribed and an expression construct (i.e., a promoter and an enhancer domain) are connected in such a way as to permit transcription of the polynucleotide in a suitable transcription medium.

By "derived from" is meant that a polynucleotide was either made or designed from a second polynucleotide, the derivative retaining important functional features of the polynucleotide from which it was made or designed. In the case of enhancer domains, the important features are specific binding to a transcription factor and conferral of neuronal cell type-specific expression when operably linked to a promoter. Optimization of binding and/or cell-specific expression may be performed.

By "expression construct" is meant a polynucleotide that is capable of directing transcription. An expression construct of the present invention includes, at the least, a multimerized enhancer domain and a promoter. Additional domains, such as a transcription termination signal, may also be included, as described herein.

By "vector" or "expression vector" is meant an expression system (e.g., an adenoviral expression system), a nucleic acid-based shuttle vehicle, a polynucleotide adapted for nucleic acid delivery, or an autonomous self-replicating circular DNA (e.g., a plasmid). When a vector is maintained in a host cell, the vector can either be stably replicated by the cells during mitosis as an autonomous structure, incorporated within the genome of the host cell, or maintained in the host cell's nucleus or cytoplasm.

By "plasmid" is meant an autonomous DNA molecule capable of replication in a cell, and includes both expression and nonexpression types.

By "heterologous" is meant that the polynucleotide originates from a foreign source or, if from the same source, is modified from its original form. Thus, a "heterologous promoter" is a promoter not normally associated with the multimerized enhancer domain of the present invention. Similarly, a heterologous polynucleotide that is modified from its original form or is from a source different from the source from which the promoter to which it is operably linked was derived.

By "transgene" is meant any piece of a polynucleotide (for example, DNA) which is inserted by artifice into a cell, and becomes part of the organism (integrated into the genome or maintained extrachromosomally) which develops from that cell. Such a transgene may include a gene that is partly or entirely heterologous (i.e., foreign) to the transgenic organism, or may represent a gene homologous to an endogenous gene of the organism.

Other features and advantages of the invention will be apparent from the following description of the preferred embodiments thereof.

DETAILED DESCRIPTION OF THE INVENTION

Figure 1:
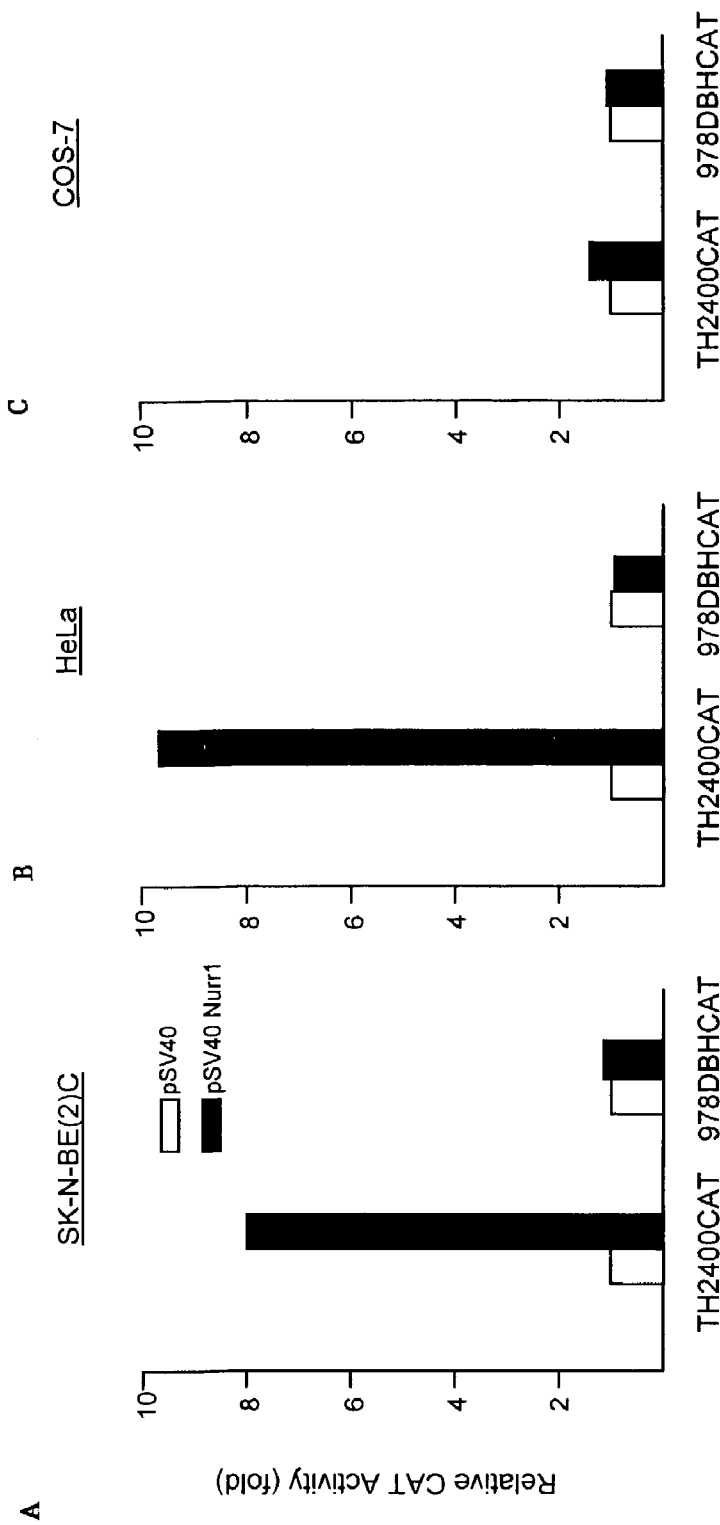
FIGS. 1A-1C are a series of schematic illustrations showing that Nurr1 robustly transactivates the promoter activity of the TH gene, but not that of the dopamine beta-hydroxylase (DBH) gene in in SK-N-BE(2)C and HeLa cell lines (FIGS. 1A and 1B, respectively). Nurr1 does not affect the promoter activity of either gene in Cos-7 cells (FIG. 1C).

We have discovered that the Nurr1 transcription factor is capable of binding to three elements proximal to the transcriptional start site of the tyrosine hydroxylase (TH) gene, and can directly control dopaminergic cell-specific TH promoter activity. Multimerization of any of these three Nurr1-responsive elements greatly increased the promoter activity of a minimal TH promoter in cell lines cotransfected with a Nurr1 expression vector, indicating that enhanced transgene expression can be obtained specifically in dopaminergic cells.

Several studies have shown that Nurr1 and a second transcription factor, Ptx3, are each required for proper development and phenotypic specification of dopaminergic neurons. Based on this similar property between Nurr1 and Ptx3, we propose that multimerization of Ptx3 responsive elements will also enhance the promoter activity in dopaminergic cells. Combinations of multiple Nurr1-responsive elements and multiple Ptx3 responsive elements will likely also likely enhance dopaminergic cell-specific transgene expression.

We also propose that this concept can be generalized to enhance gene expression in any cell type. For example, other cell type-specific enhancer elements include: 5'-TC-CCTCCC-3' (SEQ ID NO: 5), derived from insulin receptor (liver) and recognized by a 35-kDa nuclear protein, named HTFIR (hepatocyte-specific transcription factor of the insulin receptor gene); 5'-GGTTAATNATTAACA/C-3' (SEQ ID NO: 6), derived, e.g., from Alb, α1-AT, AFP, aldB, α,β-fibrinogen, aminopeptidase N, Apo-A2, ApoB, C-reactive protein, IGFBP1, hepatitis B virus, pepcK, PK, TTR, vitellogenin, or HNF4, and recognized by HNF1 (liver); 5'-A(A/T)TRTT(G/T)RYTY-3' (SEQ ID NO: 7), derived, e.g., from Alb, α1-AT, AFP, -AldB, ApoB, C7αH, TAT, transferrin, TTR, HNF3β, or HNF1, and recognized by HNF3 (liver-enriched); 5'-GGGTCAAAGGTAC-3' (SEQ ID NO: 8), derived from α1-AT, ApoCIII, ApoB, ApoA1, factor IX, X, VII, pepcK, PK, transferrin, TAT, TTR, OTC, CRBPII, or HNF1, and recognized by HNF4/LFA1 (liver-enriched); 5'-RTTAYGTAAR-3' (SEQ ID NO: 9), derived from Alb, pepcK, AldB, C7αH, CYP2C6, or vitellogenin, and recognized by PAR subfamily proteins (DBP, HLF, and VBP/TEF) (liver-enriched); 5'-CACGGGGCACTCCCGTG-3' (SEQ ID NO: 10), derived, e.g., from liver-type pyruvate kinase and recognized by ChREBP, a glucose-responsive transcription factor which is enriched in liver; the AT-rich region of the rat pro-opiomelanocortin gene (−202/−193; −262/−253), recognized by PP1 (pituitary specific); CC(A/T)$_6$GG (SEQ ID NO: 12), derived, e.g., from cardiac, skeletal, and smooth muscle α-actins, dystrophin, myosin light chain, and recognized by serum response factor (muscle specific); 5'-(C/T)TAAAAATA AC(C/T)$_3$-3' (SEQ ID NO: 13), derived, e.g., from myosin light chain 2A (muscle-specific); 5'-CANNTG-3' (SEQ ID NO: 14), derived, e.g., from creatine kinase (muscle specific); 5'-CATTCCT-3' (SEQ ID NO: 15), derived, e.g., from skeletal α-actin promoter, cardiac troponin T, cardiac α- and β-myosin heavy chain) and recognized by M-CAT binding factor (muscle-specific).

In addition to the enhancer elements described above, other cell type-specific enhancer elements can be identified using standard techniques. In one example, oligonucleotide site selection is used to identify an enhancer domain recognized by a cell-type specific transcription factor. Oligonucleotide selection can be performed with an oligonucleotide containing a randomized sequence of about 12 to 16 nucleotides flanked on both sides by about 15 bases or more of specific sequences. The single-stranded oligonucleotide is converted to double-strand DNA by klenow filling-in reaction using a primer hybridizing the specific sequence at the 3' end of the oligonucleotide. This double-stranded DNA is labeled, for example, with a radioactive deoxynucleotide during the filling-in reaction, and used as a probe in gel shift assays. Briefly, the probe is incubated with a purified cell-type specific transcription factor, and resolved on polyacrylamide gel. The DNA in the bound complexes are identified by autoradiography, extracted from the gel, and amplified using PCR. The amplified DNA is gel purified, radiolabeled with kinase, and used as a probe for another round of gel shift assay. The selection procedure is repeated for a total of about five rounds. After the last round of PCR amplification, the gel-purified DNA is cloned into a vector and sequenced.

Using the foregoing methods, one can produce multimerized enhancer domains for expression of transgenes in tissues such as the pituitary gland, liver, kidney, and heart.

Cell-specific enhancer domains can also be identified from a gene expressed in a cell-type specific manner. The identification and localization of enhancer domains in the 5' regulatory region typically begins with the analysis of nested sets of deletions in the regulatory sequences that penetrate into the region of interest from the upstream and downstream directions. The regulatory regions truncated by deletions can be analyzed, for example, in cell lines containing trans-acting factors for the enhancer domains. For comparisons, the promoters are typically also analyzed in cell lines that do not have the trans-acting factors as the negative cell line. The DNA sequences, the deletion of which down-regulates the promoter activity only in the cell lines that harbor the trans-acting factors, are then identified as containing one or more cell-specific enhancer domains. These analyses allow the outer borders of the enhancer domains to be defined and open the way to more fine mapping. As a next step, enhancer domains can be more precisely mapped by linker-scanning mutagenesis and/or site-directed mutagenesis approaches.

Multimerized Enhancer Domains

In one embodiment, the invention features multimerized enhancer domains for the specific and robust expression of genes in subtypes of neurons. The choice of an enhancer domain will depend on the neuronal subtype in which expression is desired. For example, multimerized enhancer domains for expression in dopaminergic cells can be derived from TH genomic sequence. Taking the first nucleotide of the mRNA as position +1, dopaminergic enhancer domains can include sequences located, for example, from about −873 to −866, −351 to −344, and −35 to −28. It will be understood that, for any of these dopaminergic enhancer domains, the nucleotide positions can be altered by about five to ten base pairs without substantially altering the transcription-enhancing ability of an enhancer domain. The enhancer domain that is multimerized will usually be about 7 to 40 bp in length. In addition to the multimerized dopaminergic cell-specific enhancer domains described herein, the invention features enhancer domains that are variants or modifications of these enhancer domains, as well as multimerized enhancer domains for transgene expression in, for example, other neuronal cell types, as described herein. For example, one or more nucleotides of the enhancer domain can be altered, using standard techniques, without altering transcription factor-specific binding or cell-specific expression. Using techniques described herein, one can readily ascertain whether any alteration of an enhancer domain results in either altered binding or expression.

We have now discovered that one property that results in dopaminergic cell-specific expression is binding to Nurr1. Based on our findings, we can generate, using standard techniques such as PCR or oligonucleotide synthesis, artificial enhancer domains that specifically bind to Nurr1 and increase promoter activity specifically in dopaminergic cells. Thus, any multimerized enhancer domain that specifically binds Nurr1 is considered part of the invention.

Preferably, the multimerized enhancer domain is incorporated into an enhancer cassette having the formula $(X-Y)_n$, wherein X corresponds to a cell-specific enhancer (e.g., a dopaminergic cell-specific enhancer), Y is absent or is a mono or polynucleotide that has between one and thirty nucleotides, and n is an integer between 3 and 50 inclusive (preferably between 8 and 16). It is understood that n can be even greater than 50 (e.g., 100, 200, 500, or more). In various embodiments, each X can be independently selected from the group consisting of 5'-TTCAGCCTGGCCTTTAAAGA-3' (SEQ ID NO: 1), 5'-TGTCTCCAAAGGT TATAGTT-3' (SEQ ID NO: 2), 5'-AAACAAAAGGTCACTTACTG-3' (SEQ ID NO: 3), and 5'-TAATCC(A/C)-3' (SEQ ID NO: 4). In other embodiments, X has greater than 70%, 80%, 85%, 90%, or 95% sequence identity to SEQ ID NO: 1, SEQ ID NO: 2, or SEQ ID NO: 3 and binds to Nurr1. In still other embodiments, X has greater than 70%, 80%, 85%, 90%, or 95% sequence identity to SEQ ID NO: 4 and binds to Ptx3.

Expression Constructs

Figure 7:
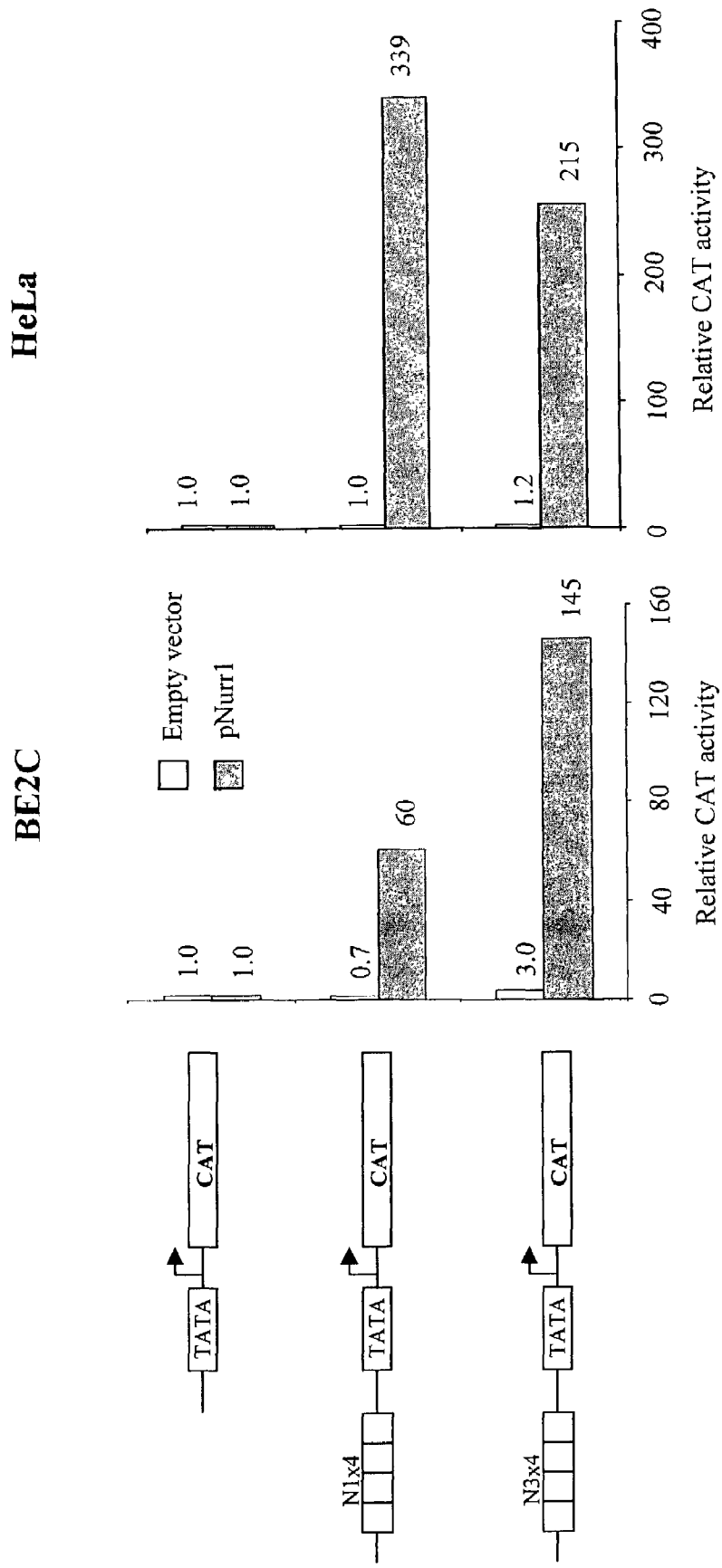
FIG. 7 is a schematic illustration showing that synthetic expression constructs containing four copies of N1 or N3 are upregulated by Nurr1 in BE2C and HeLa cells.

In one particular embodiment of the present invention, the multimerized enhancer domains or enhancer cassettes are placed in the proximity of a promoter; together, these form an expression construct. An exemplary expression construct is shown in FIG. 7.

An enhancer domain is cis-acting and desirably is located within about 5 kb, typically about 2 kb, more typically adjacent to or within about 1 kb or even 500 bp of a promoter to be enhanced. The combination of the multimerized enhancer domain and the promoter is considered to be an "expression construct." In the expression construct, the enhancer domains may be in either orientation with respect to each other as well as to the promoter, and can be located 5' or 3' in relation to the promoter they enhance, usually in the 5' direction.

A multimerized enhancer domain finds use with a wide variety of promoters, including promoters that are naturally found under the control of the enhancer, i.e., in a cis position (adjacent and homologous) and those not normally associated with the particular promoter (i.e., heterologous).

The promoter may be derived from the same or different kingdom, family, or species as the multimerized enhancer domains. Sources of promoters include viruses, prokaryotes and eukaryotes, such as bacteria, plants, insects, and mammals.

In addition to the aforementioned multimerized enhancer domain and promoter, the expression constructs may also include regulatory control regions that are generally present in the 3' regions of human genes. For example, a 3' terminator region may be included in the expression vector to increase stability of the mRNA.

Expression Vectors

In addition to an expression construct, an expression vector typically contains a dominant selectable marker gene used to identify those cells that have become transformed. Useful selectable genes include genes encoding antibiotic resistance genes, for example, those encoding resistance to hygromycin, kanamycin, bleomycin, G418, streptomycin, or spectinomycin. Alternatively, the green-fluorescent protein from the jellyfish *Aequorea victoria* may be used as a selectable marker.

The invention also contemplates DNA constructs in which an expression construct, including a multimerized cell-specific enhancer domain and a promoter, is operably linked to a polynucleotide one wishes to be transcribed. The polynucleotide may have a natural open reading frame (ORF), as well as transcribed 5' and 3' sequences flanking the ORF. Alternatively, it may be in the "antisense" orientation in that it encodes the complement of an RNA molecule or portion thereof. When the construct includes an ORF (which encodes a polypeptide), an enhanced transcription initiation rate is obtained, usually providing an increased amount of the polypeptide. For protein production, translational initiation sequences (including a start codon) are included in the constructs, either from the promoter domain, from the attached coding sequences, or from a heterologous source. When the construct contains an antisense sequence, complementary to the wild-type molecule, decreases the amount of polypeptide product. The polynucleotides of interest that are transcribed will be of at least about 8 bp, usually at least about 12 bp, more usually at least about 20 bp, and may be one kb or more in length.

Methods for Making Multimerized Enhancer Domains

A variety of multimerized enhancer domains can be produced using standard molecular biology techniques. For example, a multimerized enhancer can be constructed by first mapping restriction enzyme sites in the TH genomic sequence that includes the enhancer domain of interest, then, using the constructed map to determine the appropriate restriction enzymes, excising the domain of interest and recombining it to form a multimerized enhancer domain. Alternatively, a multimerized enhancer domain or an expression construct of the present invention can be synthesized by a variety of methods based on the sequences described herein. Synthesis can be accomplished by chemical synthesis methods for the production of enhancer oligonucleotides. In addition, a polynucleotide can be prepared by the synthesis of a series of oligonucleotides which correspond to different portions of the polynucleotide, and which can be combined by ligation to form larger polynucleotides. Finally, oligonucleotides can be used as primers in a polymerase chain reaction (PCR) to amplify a polynucleotide of interest. The primers can further contain restriction sites to facilitate ligation of the PCR fragments.

The expression constructs are typically prepared employing cloning vectors, where the sequences may be naturally occurring, mutated sequences, synthetic sequences, or combinations thereof. The cloning vectors are well known and include prokaryotic or eukaryotic replication systems, markers for selection of transformed host cells, and unique dual restriction sites for insertion or substitution of sequences.

EXAMPLE

Figure 2:
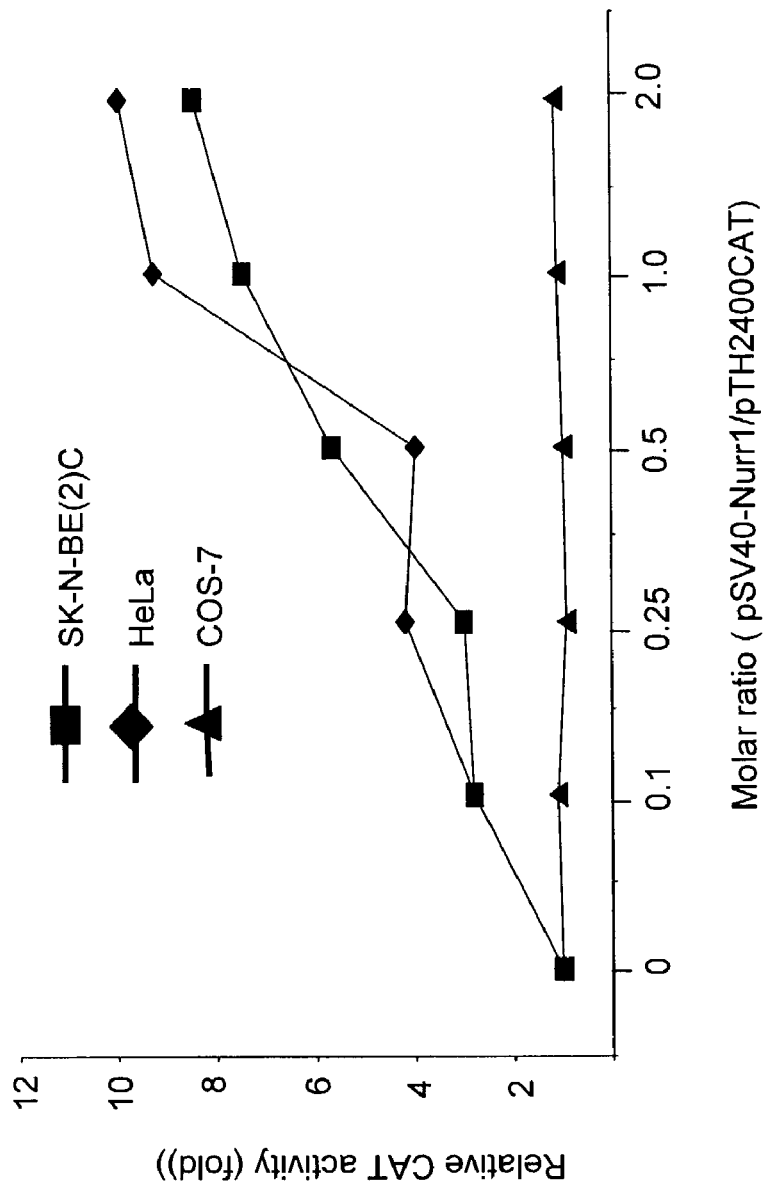
FIG. 2 is a schematic illustration showing that Nurr1 activates the promoter activity of the TH gene in a concentration-dependent manner.

Using the methods described below, we found that Nurr1 robustly transactivates the promoter activity of the TH gene, but not that of the dopamine beta-hydroxylase (DBH) gene in in SK-N-BE(2)C and HeLa cell lines (FIGS. 1A and 1B, respectively). Nurr1 does not affect the promoter activity of either gene in Cos-7 cells (FIG. 1C). Nurr1 activates the promoter activity of the TH gene in a concentration-dependent manner (FIG. 2).

Figure 3:
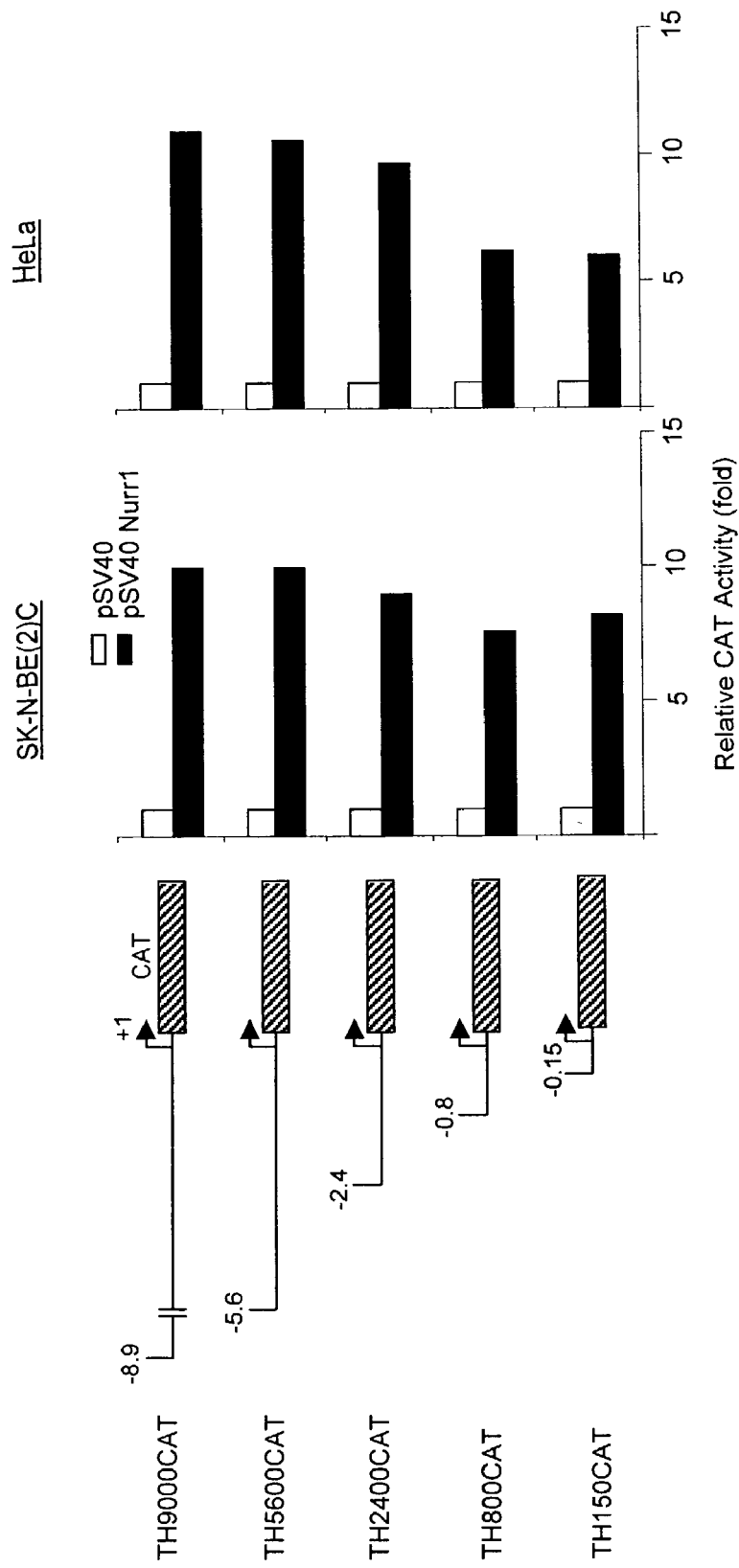
FIG. 3 is a schematic illustration showing deletional analysis of the TH 5' regulatory sequence. The proximal 150 bp upstream of the TH gene retains most of the responsiveness to Nurr1 transactivation.

We performed a deletional analysis of the TH 5' regulatory sequence, and found that the proximal 150 bp upstream of the TH gene retains most of the responsiveness to Nurr1 transactivation (FIG. 3).

Figure 4:
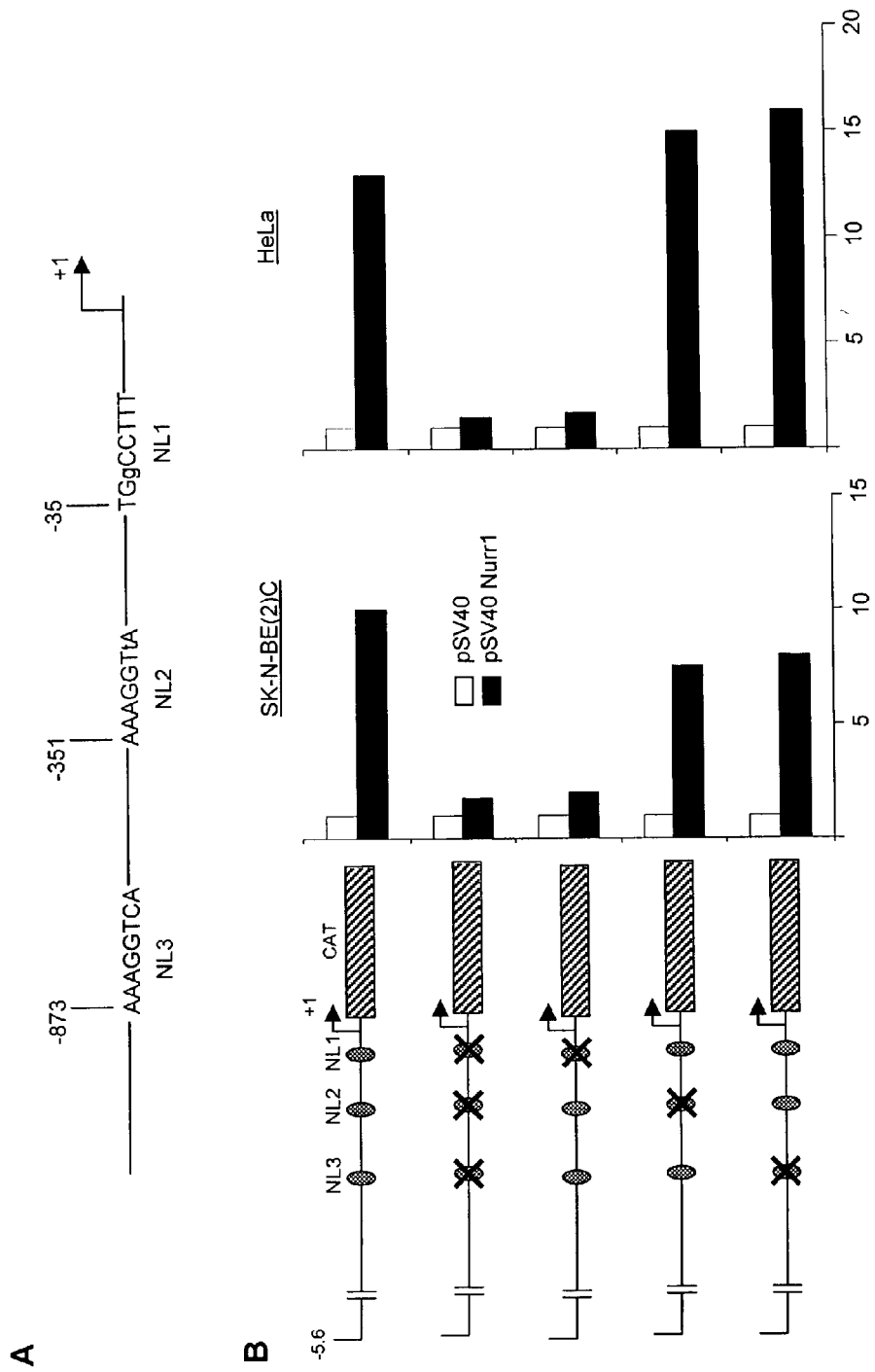
FIG. 4A is a schematic illustration showing three potential Nurr1-binding sites proximal to the transcriptional start site. While NL3 shows a perfect match with a known Nurr-1 binding motif, NL1 and NL2 each have a single base deviation from the consensus motif.
FIG. 4B is a schematic illustration showing that deletion of NL1 results in the loss of the majority of Nurr1-mediated transactivation of the promoter activity of the TH gene.

Three potential Nurr1-binding sites (NL1, NL2, and NL3) were identified proximal to the transcriptional start site (FIG. 4A). While NL3 shows a perfect match with a known Nurr-1 binding motif, NL1 and NL2 each have a single base deviation from the consensus motif. Deletion of NL1 results in the loss of the majority of Nurr1-mediated transactivation of the promoter activity of the TH gene (FIG. 4B).

Figure 5:
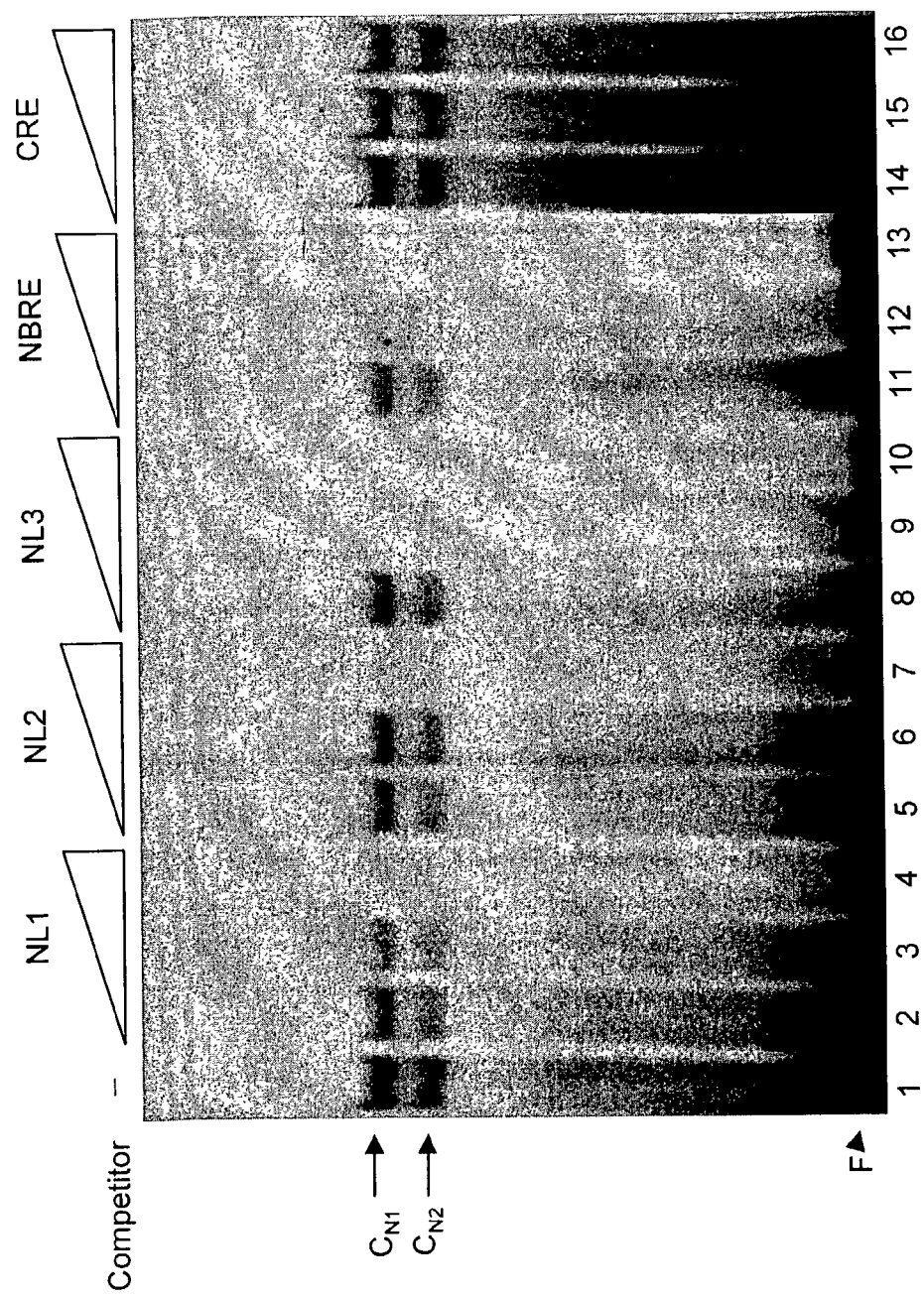
FIG. 5 is a schematic illustration showing that in vitro translated Nurr1 protein binds to a consensus binding motif (NBRE) and generates two specific DNA-protein complexes (CN1 and CN2) (lane 1). Formation of these complexes is inhibited by the presence of molar excess of its own (NBRE) or related sequences (NL1, NL2, NL3), but not by the presence of unrelated oligonucleotide CRE.

Nurr1 protein translated in vitro binds to a consensus binding motif (NBRE) and generates two specific DNA-protein complexes (CN1 and CN2) (FIG. 5; lane 1). Formation of these complexes is inhibited by the presence of molar excess of its own (NBRE) or related sequences (NL1, NL2, NL3), but not by the presence of unrelated oligonucleotide CRE.

Figure 6:
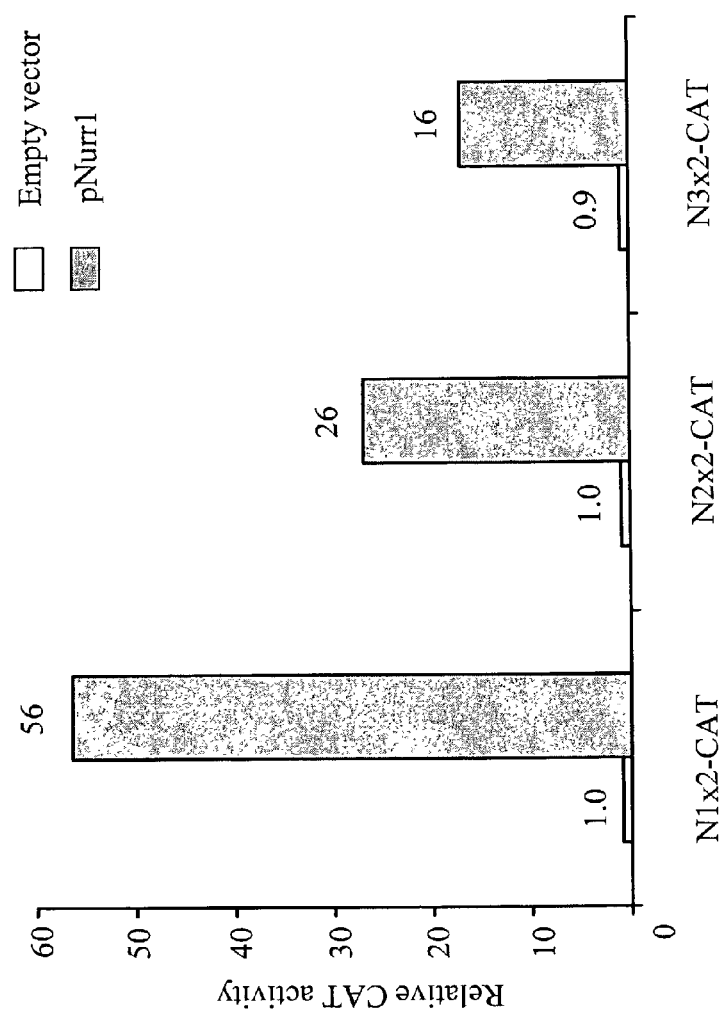
FIG. 6 is a schematic illustration showing synthetic expression constructs containing two copies of N1, N2, or N3 are upregulated by Nurr1 in HeLa cells.

Synthetic expression constructs containing two copies of N1, N2, or N3 are upregulated by Nurr1 in HeLa cells (FIG. 6). Synthetic expression constructs containing four copies of N1 or N3 are upregulated by Nurr1 in BE2C and HeLa cells (FIG. 7).

The foregoing results were obtained with the following methods.

Cell Culture and Transient Transfection Assays

Cell lines were maintained using standard techniques. Human neuroblastoma SK-N-BE(2)C, HeLa, and Cos7 cells were each grown in DMEM supplemented with 10% fetal bovine serum (Hyclone), streptomycin, and penicillin. The cells were incubated at 37° C. under 5% $CO_2$ environment. Transfection was performed by the calcium phosphate coprecipitation method as previously described (Ishiguro, supra; Seo et al., J. Neurosci., 16:4102-4112, 1996). Plasmids used for transient transfection assays were prepared using Qiagen columns (QIAGEN Inc., Santa Clarita, Calif.).

DNA Constructions

TH2400CAT was generated by inserting BglII-BamHI genomic fragment ranging from −2400 to −503 into the BamHI site of TH503CAT. TH9000CAT was constructed by replacing the 1.6-kb HindIII-XhoI DNA fragment of TH2400CAT by the 8.3-kb HindIII-XhoI DNA fragment of pTH9.0 (Min et al., Mol. Brain Res. 27:281-289, 1994). TH5600CAT was generated by deleting a 3.4-kb SphI DNA fragment from TH9000CAT. 978DBHCAT is described in Seo et al., J. Neurosci., 16:4102-4112, 1996. TH365CAT and TH150CAT are described in Kim et al., J. Biol. Chem., 268: 15689-15695, 1993. pSV40 and pSV40-Nurr1 were obtained from Dr. Conneely at Baylor College of Medicine, Houston, Tex. N1x2CAT, N2x2CAT, N3x2CAT, N1x4CAT, N3x4CAT were made as follows. Both sense and antisense oligonucleotides containing two or four copies of NL1 (−35/−28 of TH regulatory region), NL2 (−351/−343), or NL3 (−873/−866) were annealed to generate double strand DNAs. The annealed DNAs were kinased, and inserted upstream of the TATA box of TATA-CAT.

Transient Transfection Assays

Transfection was performed by the calcium phosphate precipitation method. For the SK-N-BE(2)C cells, each 60 mm dish was transfected with 2 µg of the reporter construct, 1 µg of pRSV-β-galactosidase, varying amount of the effect plasmid, and pUC19 plasmid to a total of 5 µg DNA. For HeLa and Cos7 cells, twice the amount of DNA was used per transfection. To correct for differences in transfection efficiencies among different DNA precipitates, chloramphenicol acetyltransferase (CAT) activity was normalized to that of β-galactosidase.

Multimerized Enhancer Domains

Three putative Nurr1-responsive elements found in rat TH promoter (5'-TTCAGCCTGGCCTTTAAAGA-3' (SEQ ID NO: 1); N1), 5'-TGTCTCCAAAG GTTATAGTT-3' (SEQ ID NO: 2); N2, and 5'-AAACAAAAGGTCACTTAC TG-3' (SEQ ID NO: 3; N3) were each inserted into a minimal promoter as two tandem copies. The HeLa Cells in each 60 mm dish were co-transfected with an equimolar amount of the reporter plasmids (0.5 pmol) and effector plasmids (0.5 pmol), 1.5 µg of pRSV-β-gal (for normalization of transfection efficiency), and pUC19 to a total of 6 µg. Two days after transfection, cells were lysed and assayed for CAT and β-galactosidase activities. CAT activity was normalized first to β-galactosidase activity for each experiment, and this normalized CAT activity was used to compare promoter activity between experiments.

What is claimed is:

1. An expression vector comprising
   (i) an enhancer cassette having the formula $[X-Y]_n$, wherein each X is independently a polynucleotide consisting of the sequence of SEQ ID NO: 3; Y is absent or is a mono- or polynucleotide that has between one and thirty nucleotides; and n is an integer between five and fifty, inclusive;
   (ii) an RNA polymerase binding site;
   (iii) a transcription initiation site; and
   (iv) a polynucleotide to be expressed,
wherein said enhancer cassette, RNA polymerase binding site, transcription initiation site, and polynucleotide are spatially arranged in said vector such that said polynucleotide is capable of being expressed when said vector is in a dopaminergic cell.

2. An enhancer cassette having the formula $[X-Y]_n$, wherein each repeated X subunit, independently, is the polynucleotide consisting of the sequence of SEQ ID NO: 3; each repeated Y subunit, independently, is a polynucleotide containing between zero and thirty nucleotides; and n is an integer between five and fifty, inclusive.

3. The cassette of claim 2, wherein n is eight or greater.

4. The cassette of claim 3, wherein n is ten or greater.

5. The cassette of claim 4, wherein n is fifteen or greater.

* * * * *

SEQUENCE LISTING

```
<160> NUMBER OF SEQ ID NOS: 14

<210> SEQ ID NO 1
<211> LENGTH: 20
<212> TYPE: DNA
<213> ORGANISM: Mus musculus

<400> SEQUENCE: 1
ttcagcctgg cctttaaaga                                              20

<210> SEQ ID NO 2
<211> LENGTH: 20
<212> TYPE: DNA
<213> ORGANISM: Mus musculus

<400> SEQUENCE: 2
tgtctccaaa ggttatagtt                                              20

<210> SEQ ID NO 3
<211> LENGTH: 20
<212> TYPE: DNA
<213> ORGANISM: Mus musculus

<400> SEQUENCE: 3
aaacaaaagg tcacttactg                                              20

<210> SEQ ID NO 4
<211> LENGTH: 7
<212> TYPE: DNA
<213> ORGANISM: Artificial Sequence
<220> FEATURE:
<221> NAME/KEY: misc_feature
<222> LOCATION: 7
<223> OTHER INFORMATION: n = A or C
<220> FEATURE:
<223> OTHER INFORMATION: Consensus
```

-continued

```
<400> SEQUENCE: 4 taatccn                                                                    7

<210> SEQ ID NO 5
<211> LENGTH: 8
<212> TYPE: DNA
<213> ORGANISM: Homo sapiens

<400> SEQUENCE: 5 tccctccc                                                                   8

<210> SEQ ID NO 6
<211> LENGTH: 15
<212> TYPE: DNA
<213> ORGANISM: Artificial Sequence
<220> FEATURE:
<221> NAME/KEY: misc_feature
<222> LOCATION: 8
<223> OTHER INFORMATION: n = A,T,C, or G
<221> NAME/KEY: misc_feature
<222> LOCATION: 15
<223> OTHER INFORMATION: n = A or C
<220> FEATURE:
<223> OTHER INFORMATION: Consensus

<400> SEQUENCE: 6
ggttaatnat taacn                                                          15

<210> SEQ ID NO 7
<211> LENGTH: 11
<212> TYPE: DNA
<213> ORGANISM: Artificial Sequence
<220> FEATURE:
<221> NAME/KEY: misc_feature
<222> LOCATION: 2
<223> OTHER INFORMATION: n = A or T
<221> NAME/KEY: misc_feature
<222> LOCATION: 7
<223> OTHER INFORMATION: n = T or G
<220> FEATURE:
<223> OTHER INFORMATION: Consensus

<400> SEQUENCE: 7
antrttnryt y                                                              11

<210> SEQ ID NO 8
<211> LENGTH: 13
<212> TYPE: DNA
<213> ORGANISM: Artificial Sequence
<220> FEATURE:
<223> OTHER INFORMATION: Consensus

<400> SEQUENCE: 8
gggtcaaagg tac                                                            13

<210> SEQ ID NO 9
<211> LENGTH: 10
<212> TYPE: DNA
<213> ORGANISM: Artificial Sequence
<220> FEATURE:
<223> OTHER INFORMATION: Consensus

<400> SEQUENCE: 9 rttaygtaar                                                                10

<210> SEQ ID NO 10
```

```
<211> LENGTH: 17
<212> TYPE: DNA
<213> ORGANISM: Mus musculus

<400> SEQUENCE: 10
cacggggcac tcccgtg                                                  17

<210> SEQ ID NO 11
<211> LENGTH: 10
<212> TYPE: DNA
<213> ORGANISM: Artificial Sequence
<220> FEATURE:
<221> NAME/KEY: misc_feature
<222> LOCATION: 3, 4, 5, 6, 7, 8
<223> OTHER INFORMATION: n = A or T
<220> FEATURE:
<223> OTHER INFORMATION: Consensus

<400> SEQUENCE: 11 ccnnnnnngg                                                          10

<210> SEQ ID NO 12
<211> LENGTH: 14
<212> TYPE: DNA
<213> ORGANISM: Artificial Sequence
<220> FEATURE:
<221> NAME/KEY: misc_feature
<222> LOCATION: 1, 12, 13, 14
<223> OTHER INFORMATION: n = T or C
<220> FEATURE:
<223> OTHER INFORMATION: Consensus

<400> SEQUENCE: 12
ntaaaaataa cnnn                                                     14

<210> SEQ ID NO 13
<211> LENGTH: 6
<212> TYPE: DNA
<213> ORGANISM: Artificial Sequence
<220> FEATURE:
<221> NAME/KEY: misc_feature
<222> LOCATION: 3, 4
<223> OTHER INFORMATION: n = A,T,C, or G
<220> FEATURE:
<223> OTHER INFORMATION: Consensus

<400> SEQUENCE: 13 canntg                                                              6

<210> SEQ ID NO 14
<211> LENGTH: 7
<212> TYPE: DNA
<213> ORGANISM: Artificial Sequence
<220> FEATURE:
<223> OTHER INFORMATION: Consensus

<400> SEQUENCE: 14 cattcct                                                             7
```